(12) United States Patent
Seex

(10) Patent No.: US 11,723,643 B2
(45) Date of Patent: Aug. 15, 2023

(54) DISTRACTION AND RETRACTION ASSEMBLY INCORPORATING LOCKING FEATURE

(71) Applicant: Retrospine Pty Ltd, Kingswood (AU)

(72) Inventor: Kevin Seex, Kingswood (AU)

(73) Assignee: RETROSPINE PTY LTD, Nsw (AU)

( * ) Notice: Subject to any disclaimer, the term of this patent is extended or adjusted under 35 U.S.C. 154(b) by 497 days.

(21) Appl. No.: 17/018,391

(22) Filed: Sep. 11, 2020

(65) Prior Publication Data
US 2021/0128131 A1    May 6, 2021

(30) Foreign Application Priority Data
Sep. 12, 2019  (AU) .................................. 2019903392

(51) Int. Cl.
*A61B 17/70* (2006.01)
*A61B 17/02* (2006.01)

(52) U.S. Cl.
CPC ........ *A61B 17/025* (2013.01); *A61B 17/0206* (2013.01); *A61B 17/7076* (2013.01); *A61B 2017/0256* (2013.01)

(58) Field of Classification Search
CPC .......... A61B 17/025; A61B 2017/0256; A61B 17/0206; A61B 17/7076

USPC .......................................................... 606/90
See application file for complete search history.

(56) References Cited

U.S. PATENT DOCUMENTS 10,314,624 B2 * 6/2019 Chao .................... A61B 17/708
2009/0281579 A1 * 11/2009 Weaver .............. A61B 17/7076
606/301

* cited by examiner

*Primary Examiner* — Eduardo C Robert
*Assistant Examiner* — Christina Negrellirodriguez
(74) *Attorney, Agent, or Firm* — Stephen J. Weyer, Esq.; Stites & Harbison, PLLC

(57) ABSTRACT

A device for use in a surgical distraction and retraction assembly, the assembly including the device and at least one bone anchoring pin for securing the device against a bearing surface. The device has an integral frame defining an internal space, the frame having a first pair of opposing side arms and a second pair of opposing side arms. At least one of said side arms of said first pair of opposing side arms including at least one recess each having one of its ends open to the internal space defined by the frame and an opposite closed end terminating within said at least one side arm. Each said recess retains one said at least one bone anchoring pin and is configured to enable relative movement between the frame and the bone anchoring pins. The relative movement allows selective locking of said at least one anchor pin against the frame at a user selected location to maintain a selected extent of vertebral distraction.

17 Claims, 6 Drawing Sheets

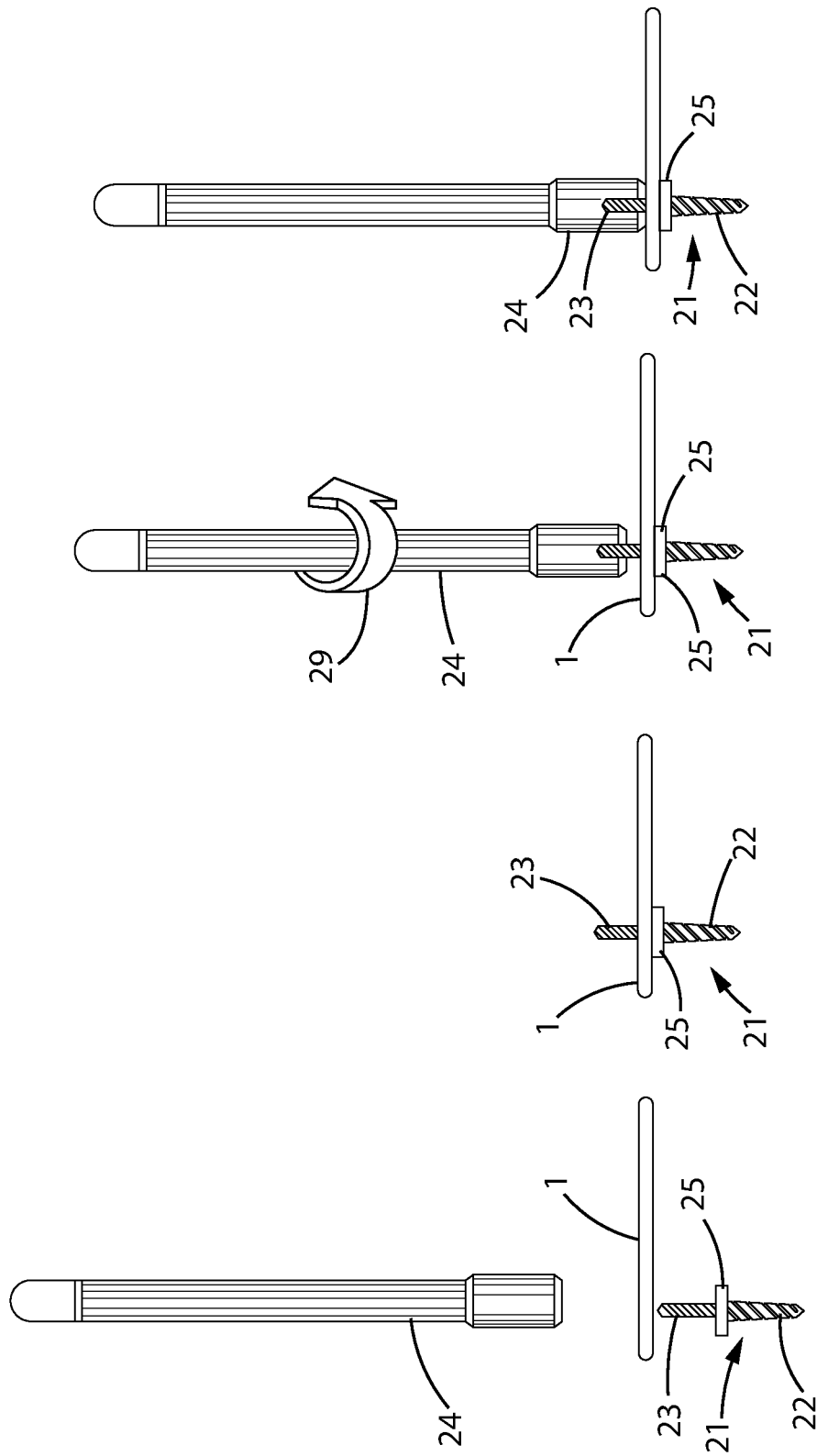

DISTRACTION AND RETRACTION ASSEMBLY INCORPORATING LOCKING FEATURE

BACKGROUND

The present invention relates to bone distraction and retraction assemblies used in bone surgery. More particularly, the invention relates to a distracter locking mechanism and method which enables selection of an extent of bone distraction and locking of the selected distraction. The invention further provides a locking mechanism which allows anchor pins attached to spaced apart vertebrae to be set and maintained at a selected position of distraction by locking of a distraction assembly at a preselected spacing of the vertebrae. More particularly the invention provides a lockable distraction device which also co-operates with retraction arms thereby allowing combined selection and locking of distraction and retraction.

PRIOR ART

There are in existence a number of assemblies used in distraction of bone. In particular, there is a variety of known distracters which distract vertebrae during spinal surgery. Such distraction assemblies must be maintained in a setting which maintains a predetermined distraction of vertebrae to allow a surgeon access to the disc space intermediate the vertebrae. This vertebral separation is required in cervical and lumbar spinal disc surgery.

The most commonly performed anterior cervical procedure is an intervertebral fusion procedure that typically involves the steps of removing a portion or all of affected disc material, spreading apart adjacent vertebrae with a distracter and inserting an implant bone or cage or prosthetic disc into the space previously occupied by the removed disc material. In the lumbar spine this procedure can be done either from the front of the patient (anterior interbody fusion) or from the back (posterior interbody fusion). Distraction devices are normally used in conjunction with retraction blades which keep soft tissue retracted along an axis transverse to the longitudinal axis of distraction. It is important in order to reduce trauma to soft tissues which may occur from contact with parts of distraction and retraction hardware so that the surgical procedure is as minimally invasive as possible and thus minimally interferes with and minimally traumatizes the organs, tissues and vasculature being displaced to allow access to the vertebral region being treated. Various types of distraction assemblies are known each having means to secure distracter arms at a setting which maintains a predetermined setting of vertebrae during spinal disc surgery.

By way of an example of a known distraction device, U.S. Pat. No. 6,669,699 discloses a Distraction instrument for use in anterior cervical fixation surgery. The publication teaches an intervertebral distraction tool having a clamshell head with upper and lower halves, each having a curved outer surface and a flat inner surface. The distal side of the head is hinged so that the head opens and closes from the proximal side of the head. The hinge is a separating hinge that allows the halves to not only angulate with respect to one another about the hinge axis, but also to vertically separate from one another at the hinge.

In another example U.S. Pat. No. 6,743,231 discloses temporary spinal fixation apparatuses and methods for temporarily fixing the relative position of spinal implant assemblies until a permanent fixation position is determined. The disclosed apparatuses and methods enhance the ease of placement of spinal implant assemblies and facilitate the accuracy of positioning of the spinal vertebrae.

In another example U.S. Pat. No. 6,017,342 discloses a compression and distraction instrument having two pivotally connected handles. Jaws engage objects, human bone, for purposes of manouvering. A control screw connects with the handles, through a mechanical advantage arrangement, and the screw pivots the jaw portions for the engagement of the objects. There is an anti-friction connection between the screw and the handles, for accurate and precise movement of the jaws. In one embodiment, the screw is axial of the instrument, and, in the other embodiment, the screw is transverse thereto, both have mechanical advantage.

In another example U.S. Pat. No. 6,712,825 of Mar. 30, 2004 discloses a spinal disc space distracter for separating adjacent elements, such as vertebrae. The distracter preferably has a scissors-type distracting mechanism, either in a simple scissors or double-acting scissors configuration. The distracter includes blades that are removable from the jaws of the distracter such that different blades may be used depending on the patient and situation with which the distracter is to be used. This distracter has a scissor-like configuration with a pair of handles pivotally connected together. A distracter jaw is coupled to a distal end of each handle such that movement of the handles together draws the jaws apart to separate the vertebrae being treated. A locking mechanism preferably is provided adjacent to or in the handle to maintain distraction. The locking mechanism may include a spindle or threaded bolt mounted on a first handle and passing through the second handle. An internally threaded speed nut is rotatably mounted on the threaded bolt such that movement of the speed nut along the bolt selectively inhibits movement of the second handle away from the first handle and thus maintains the vertebrae at the desired distracted position.

U.S. Pat. No. 9,980,712 to the present applicant Kevin Seex discloses a combined retraction and distraction assembly. This assembly includes anchor pins which anchor the assembly to bone. The assembly includes a two part frame formed from cooperating members, one of which is slidable relative to the other. The frame is provided in two primary parts each including support arms which attach to a retaining member. The assembly includes two bone anchorage pins and the frame assembly including each of the retaining members which respectively receive an end of retractor blade support arms and is generally U-shaped such that first and second retaining arms are parallel and includes one opening configured to receive one anchorage pin enabling fixation of the frame assembly to bone. A first bridge joins the retaining members and is integrally attached to them. Each of the retaining members have a first end attached to the first bridge and a second free end. The frame assembly has a second bridge including openings to allow engagement with said free ends of the retaining members. The first and second bridges each include an opening to allow penetration of one anchorage pin for screw fixation of the assembly to bone.

The prior art distracter assemblies have mechanisms to secure the distracter in a set position but these mechanisms generally lie outside the patients wound and inhibit access to the operating site. One example is the Caspar distraction assembly which can be locked in position by a ratchet outside the wound which transmits forces to the distraction pins inside the wound when embedded in the vertebrae. None of the prior art distraction assemblies have a locking mechanism inside the wound and require substantial hardware outside the wound taking up space which if free, would provide better access for the surgeon to the operating site. Since the prior art locking mechanisms for distracters are located outside the wound, this increases the transmission distance for locking forces required at the operating site due to a longer moment arm.

Typically according to known methodology, cervical distraction of vertebrae involves the use of pins temporarily fixed to the vertebrae to be distracted. Generally two pins are used one above and one below a disc or vertebral body of interest. Traditionally in a Caspar system these pins have only been used for distraction purposes via sliding tubes that fit axially over the pins and connect to an associated distraction mechanism. The known and commonly used Caspar type distracter is then secured to the spine. There is however known use of distracter tubes that each slide over respective pins and which is secured to the pins via a screw applied at a threaded region.

This does not provide optimal load transfer to the spinal vertebrae where distraction is required but rather applies the load at a moment arm distant from the required load application site. The known technique for distraction force application applies a bending and shear force to the pins which must be transferred down the pin to its point of engagement with the vertebrae. A mechanical advantage during distraction is provided the closer the load is applied to the vertebrae due to a reduced moment arm and elimination of a bending moment on the pins so it is desirable to provide an assembly which meets this objective.

Within the field of spinal surgery, a common procedure is excision of an intervertebral disc for the purpose of decompression of the spinal cord or nerve roots. The excised disc is then replaced with bone graft or other types of implants. In order to make this easier it is advantageous if the vertebral bodies can be held apart or even stretched further apart. This process of separating bones is termed distraction.

To accomplish this there are two commonly used techniques:
1. Intervertebral; and
2. Non-intervertebral.

Intervertebral

This involves insertion of a spreading type instrument into the excised disc space which engages the upper and lower vertebral bodies and when applied separates them. This is known as intervertebral distraction. A simpler technique is rotation of an oval shaped block. This is known as a shim distracter. Both of these provide a very strong mechanically advantageous force.

The disadvantages of these techniques includes the following: In order to maintain distraction the instruments must remain in the disc space which obscures access for the rest of the procedure. The distraction can also be asymmetrical depending on the position of the distracters within the space. The shim distracters impart a rotational or translational force to the bodies relative to one another. This can be harmful and encourage unwanted movements particularly if there some bony or ligamentous deficiency.

Non Intervertebral

This is widely used in the cervical spine using Caspar™ distracters. This requires long screws to be inserted into the upper and lower bodies. Hollow arms are slid over these arms and a distraction force applied to the bodies through the screws. The distraction mechanism is often a thumb screw along a bar with a ratchet to secure position. This mechanism sits outside the wound. One disadvantage is that the screws often bend because of the distance from the distracting force which is outside the wound to the point of contact with the bone. This creates a bending moment which bends the screws as they emerge from the bone. It also causes fish mouthing of the disc space i.e. it opens more at the front than the back.

This general mechanism has been improved in The Prodisc C™ apparatus by securing the distractor arms to the bone screw with a compression cap forcing the distractor arms downwards and lowering the point of fixation further down the screw. This widely used general Caspar technique has the advantage over the intervertebral technique in that it can be used to hold distraction. It is possible to perform distraction with the first stronger technique and hold the distraction with the second allowing removal of the intervertebral instrument for greater access to the disc space. The force required to maintain distraction of the vertebral bodies against the elastic recoil of the tissues is much less that the distraction force required to separate them initially. Once distracted there is a natural elastic recoil of the stretched tissues. The other disadvantage of both Caspar™ and Prodisc C™ second technique apart from those mentioned is that in both, the mechanisms are bulky and while outside the wound can still impede access for hands, other tools and light.

SUMMARY OF THE INVENTION

The present invention seeks to ameliorate the prior art disadvantages by providing a distraction assembly including a frame and locking mechanism inside a wound which enables a distracter assembly of the type comprising adjustable elements to be set to a selected position and locked from relative movement by a locking mechanism which directly engages the adjustable elements. The invention further provides a frame which enables bi lateral locking of anchor pins to the frame upon selection of a degree of distraction, the frame including a pair of side arms which retain retractor blades.

The present invention in one form provides improvements in distraction and retraction assemblies by allowing selective bi lateral locking of anchor pins against a frame to maintain a selected degree of distraction. Although the invention will be described with reference to its surgical applications it will be recognised by persons skilled in the art that the invention apparatuses and mechanisms have wider applications in other fields.

The present invention utilizes bone screws to maintain a distraction force with a mechanically advantageous locking mechanism. The bone screws are connected using a small internal frame that sits within the wound very close to the region where compression forces are being applied. The frame includes a first pair of side arms and a second pair of side arms. The first pair of side arms each include at least one recess or opening which allows travel therein and relative movement of an anchor pin attached to an upper vertebral body. The pins move in the recess or opening relative to the frame which is supported by a bearing surface on the pins. The vertebrae can be initially separated by a scissor distracter when the anchorage pins and frame assembly are in position.

In the cervical spine, single screws in each vertebral body are used while in the lumbar area two screws are required. The screws in each vertebral body support the respective part of the distraction frame assembly. The frame is tightened against the bearing surface of the pins using threaded tightening caps. Once the two pins are locked to the frame distraction is set. This is after a predetermined distraction setting is selected by a surgeon. It should be noted that while in this embodiment and surgical situation the apparatus acts principally as a distractor lock, it could also be used in other circumstances to prevent distraction or other unwanted movements of the two bodies relative to each other.

In one broad form the present invention comprises: a device for use in a surgical distraction and retraction assembly, the assembly including the device and at least one bone anchoring pin for securing the device against a bearing surface; characterised in that the device comprises an integral frame defining an internal space, the frame having a first pair of opposing side arms and a second pair of opposing side arms; each said arms of said first pair of opposing side arms including at least one recess each having one of its ends open to the internal space defined by the frame and an opposite closed end; each said recesses receiving one said at least one bone anchoring pin and enabling locking of said at least one anchor pin against the frame to maintain a selected degree of distraction.

According to one embodiment, each side arm of the second pair of opposing side arms each receive and retain a retractor blade. According to one embodiment, the retractor blade is capable of movement relative to and detachable attachment to and from the side arm. Preferably, the movement is rotation relative to a longitudinal axis of the mounting arm.

The closed end of each said recesses in which a pins may be inserted, provides a limiting abutment for the anchor pins enabling setting of a degree of distraction and/or degree of lordosis as required. Preferably, the frame is generally planar and includes an interior space sufficient to provide surgical access to an operation site. Locking of the frame is effected by clamping between a bearing flange on each anchor pin and a tightening nut which is tightened against an upper surface of the one or both of said first pair of side arms.

In another broad form the present invention comprises: a frame for use in a surgical distraction and retraction assembly, the assembly including the frame and at least two bone anchoring pins for securing the frame against a bearing surface on said at least two pins; characterised in that the frame, has a first pair of opposing side arms and a second pair of opposing side arms each defining an internal space; each said side arms of said first pair of opposing side arms including at least one recess having one of its ends open to the internal space and an opposite closed end; at least one of each said recesses on each of the first pair of opposing sides receiving at least one of said at least one bone anchoring pins and enabling relative movement between the bone anchoring pins and selective locking of said frame via a tightening device inducing compression against said at least two anchor pins to maintain a selected degree of distraction.

In one broad form the present invention comprises: a device for use in a surgical distraction assembly, the assembly including the device and at least two bone anchoring pins for securing the device against a bearing surface associated with the anchoring pins; characterised in that the device comprises a frame having a first pair of opposing sides and a second pair of opposing sides each defining an internal space, each said sides of said first pair of opposing sides including at least one recess each having one of its ends open to the internal space and an opposite closed end; said at least one said recess receiving one said at least one bone anchoring pin, the anchoring pins cooperating with the frame to enable selective locking of said at least one anchor pin against the frame to maintain a selected degree of distraction.

According to one embodiment the locking is effected by compression induced between the frame and each said locking pins. According to one embodiment, each side arm of said first pair of side arms has a recess of the same size. Preferably, each recess is elongated to enable relative movement between the bone anchor pins and the frame. According to one embodiment, one of said first pair of side arms has one recess and the other of said first pair of sides has two recesses of the same size and a third recess larger than the two recesses. The two recesses of the same size accommodate an anchor pin and the third larger recess accommodates at least part of a fusion plate insertable into the internal space. According to a preferred embodiment the other of said first pair of side arms includes a generally elongated recess which accommodates an anchor pin. According to a preferred embodiment, the second pair of opposing side arms include retaining arms which respectively receive and retain retractors.

Preferably, each side arm of said first pair of side opposing arms comprises a bridge which receives an anchorage pin via at least one recess. The second of said first pair of opposing side arms also includes at least one recess which receives another anchorage pin. Once the vertebral bones have been distracted into the desired position, the locking mechanism allows the anchorage assembly to be secured in a selected position. The present invention has numerous advantages over the prior art including ease of placement of the frame, increased capability of adjustment and increased potential for lordotic angulation. Throughout the description a reference to a locking nut can be taken to mean a reference to a locking cap or any other device which allows locking of the anchor pins against the frame. A reference to an anchor pin can be taken to include a reference to a reference to any bone anchor such as but not limited to a bone screw. A reference to a side arm can be taken to include a reference to a bridge or support member. Locking can be taken to include a reference to any mechanism which creates sufficient compression or friction so that relative movement between the frame and bone anchor pins is arrested.

BRIEF DESCRIPTION OF THE DRAWINGS

The present invention will now be described in more detail according to a preferred embodiment but non limiting embodiment and with reference to the accompanying illustrations.

FIG. 2 shows an exploded elevation view of the distraction assembly including the frame, bone anchor pins and locking cap.

FIG. 3 shows the assembly of FIG. 2 with the anchor pin engaged with the frame.

FIG. 4 shows the locking cap engaging the anchor pin.

FIG. 5 shows the locking cap compressed against the frame.

DETAILED DESCRIPTION

Figure 1:
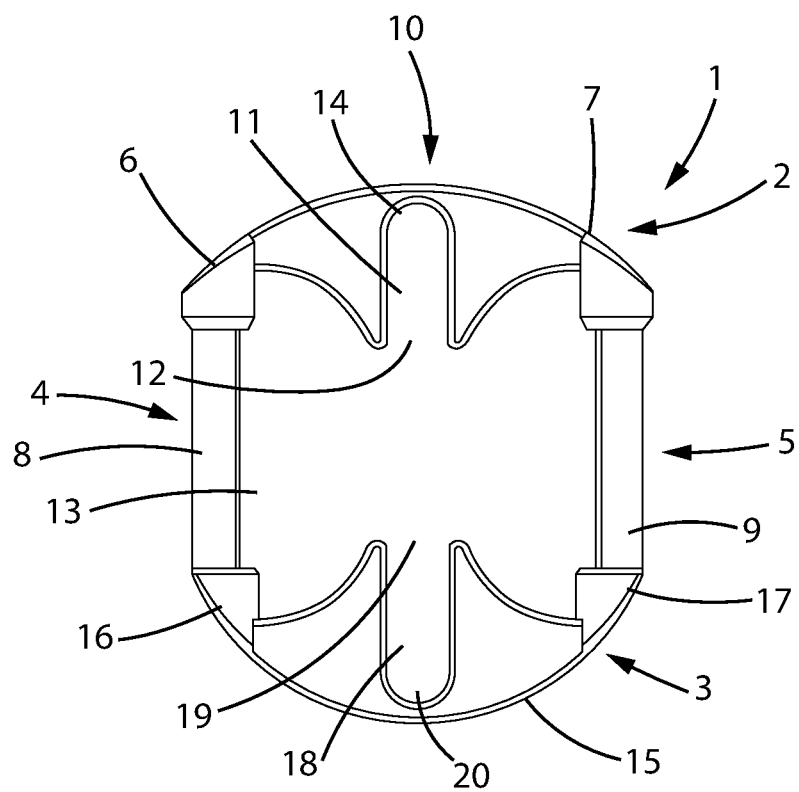
FIG. 1 shows an enlarged plan view of a frame device according to a preferred embodiment of the lockable distraction assembly.

FIG. 1 shows an enlarged plan view of a frame device 1 of the lockable distraction assembly according to a preferred embodiment. Frame 1 is in use, anchored to bone to set distraction once engaged with anchor pins to be described below. Frame 1 comprises a first pair of opposing sides 2 and 3 and a second pair of opposing sides 4 and 5 which comprise retractor blade support arms 8 and 9. Side 2 includes a bridge 10 which terminates at first and second abutments 6 and 7 which respectively engage one end of retractor support arms 8 and 9. Bridge 10 further comprises an elongated recess 11 having one end 12 open to internal space 13 and a closed end 14 which provides when frame 1 is in use, a limiting abutment for an anchor pin. Side 3 includes a bridge 15 which terminates at first and second abutments 16 and 17 which respectively engage retractor support arms 8 and 9. Bridge 15 further comprises an elongated recess 18 having one end 19 open to internal space 13 and a closed end 20 which also provides when frame 1 is in use, a limiting abutment for an anchor pin. Elongated recesses 11 and 18 allow longitudinal movement of an anchor pin along the recesses and relative to from 1 during selection of a distraction setting.

FIG. 2 shows an exploded elevation view of the distraction assembly including the frame 1, anchor pin 21 and locking cap 24. Anchor pin 21 comprises a threaded first end 22 which is anchored in vertebral bone, a second threaded end 23 which engages locking cap 24 which is rotated to compress frame 1 against flange 25 as showed in FIG. 5. Intermediate ends 22 and 23 is base plate/flange 25 which provides a bearing surface for frame 1.

FIG. 3 shows with corresponding numbering the assembly of FIG. 2 with the anchor pin 21 engaged with the frame 1. FIG. 4 shows with corresponding numbering the locking cap 24 engaging the anchor pin 21 and the anchor pin 21 engaged with frame 1. Cap 24 is rotated as indicated by arrow 29 to lock or unlock frame 1 against flange 25. Prior to this, anchor pin 21 is free to move relative to frame 1 under the action of a distraction tool until the selected extent of distraction is set.

FIG. 5 shows the locking cap 24 compressed against the frame 1.

Figure 6A:
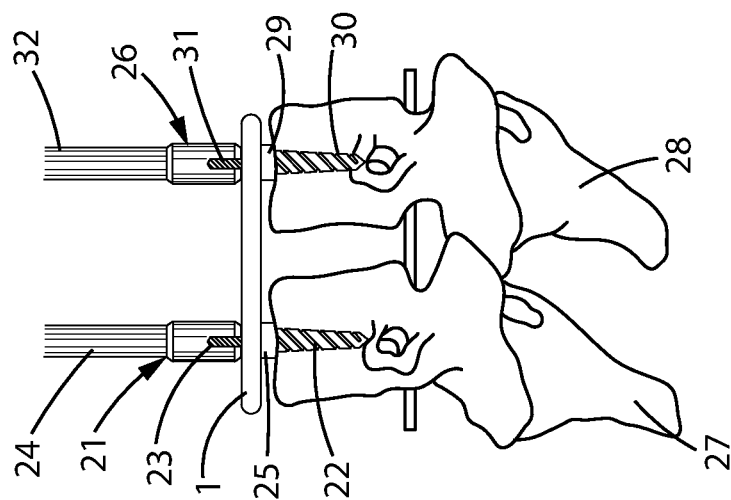
FIGS. 6a-c show elevation views of the distraction assembly including bone anchor pins in stages of set up.
Figure 6B:
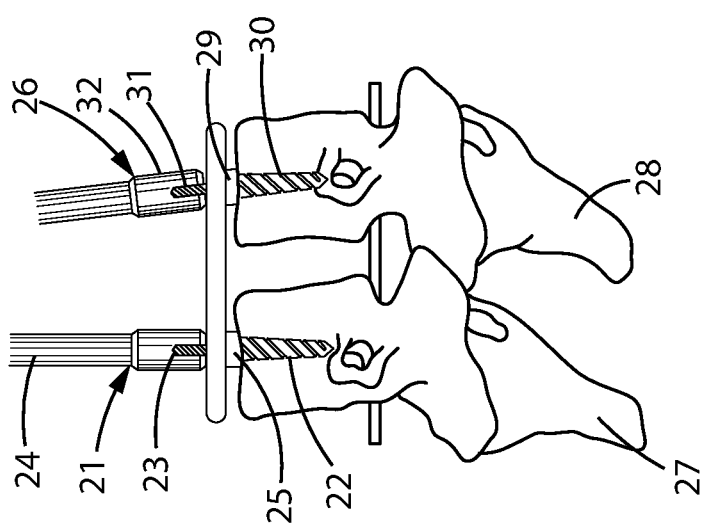
Figure 6C:
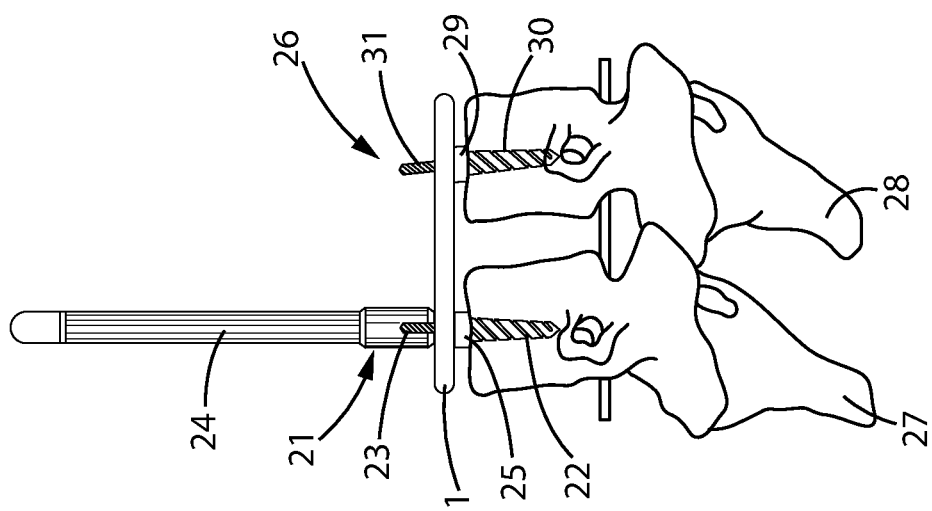

FIG. 6a-c show elevation views of the distraction assembly including bone anchor pins 21 and 26 respectively anchored to vertebrae 27 and 28 in stages of set up to locked distraction. Referring to FIG. 6a anchor pin 21 is shown inserted in a vertical alignment in vertebrae 27. As shown, pin 21 is engaged with tightening cap 24. Anchor pin 26 is inserted in vertebrae 28 via end 30 at an angle which will allow lordosis once cap 32 locks plate 1 against bearing flange 29. By placing pin 26 at a predetermined angle in vertebrae 28, the extent of lordosis can be predetermined as required by a surgeon. After locking of pin 21 to plate 1 via locking cap 24, pin 26 is locked into a vertical position. Before locking pin 26 disposed at an angle off the vertical relative to the extent of lordosis required. This is achieved by selecting an angle of deviation from a vertical reference. Prior to locking, end 31 of pin 26 is rotated back to the vertical which results in rotation of vertebrae 28 to a corresponding angle off the vertical relative to the original angle of the insertion off the vertical of pin 26.

FIG. 6b shows cap 32 engaged with pin 26 prior to locking. It can be seen that cap 32 is not parallel to cap 24 prior to locking of pin 26 to frame 1. FIG. 6c shows cap 32 rotated to the vertical and vertebrae 28 disposed at an angle off the vertical. Apart from distraction of vertebra 27 and 28, lordosis provides additional angled separation between the vertebrae which facilitates better access to the disc space.

Figure 7A:
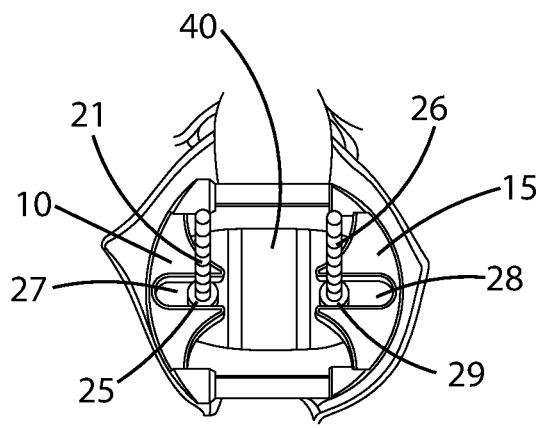
FIGS. 7a-g show step by step illustrations of the use of the distraction assembly including the frame, anchor pins and retractor blades.
Figure 7B:
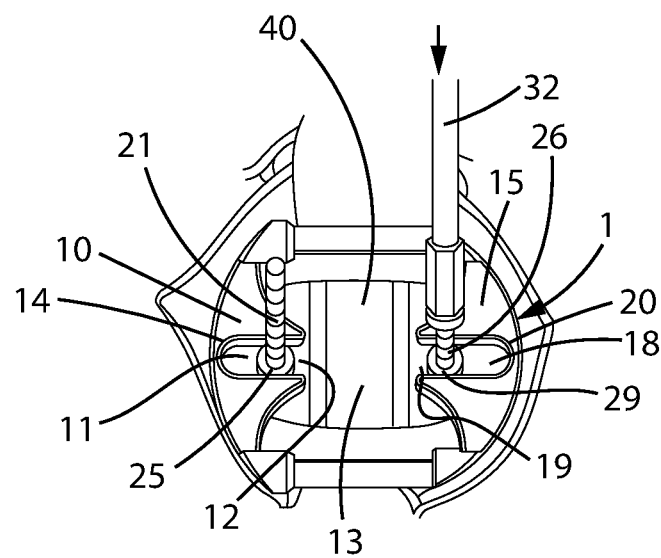
Figure 7C:
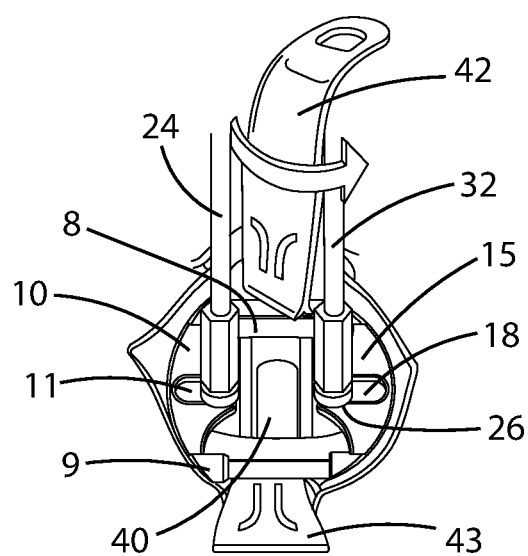
Figure 7D:
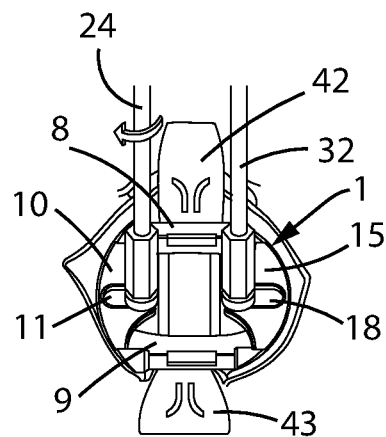

FIG. 7a-g shows with corresponding numbering for corresponding parts described earlier, step by step illustrations of the set up and use of the distraction assembly including the frame, anchor pins and retractor blades. In FIG. 7a, anchor pins 21 and 26 are shown screwed into respective vertebrae 27 and 28. Between vertebrae 27 and 28 is a disc space 40. As shown in FIG. 7b, frame 1 is fed over pins 21 and 26 and bears on base plates/flanges 25 and 29 respectively. Recess 11 of bridge 10 has one end 12 open to internal frame space 13 and a closed end 14 which provides when frame 1 is in use, a limiting abutment for an anchor pin 21. Likewise bridge 15 comprises an elongated recess 18 having one end 19 open to internal space 13 and a closed end 20 which also provides when frame 1 is in use, a limiting abutment for an anchor pin 26. FIG. 7b shows the insertion of screw on locking cap 32 over pin 26 which is left loose until retractor blades 42 and 43 (see FIG. 7c) are positioned on support arms 8 and 9. FIG. 7c shows retractor blades 42 and 43 respectively engaging support side arms 8 and 9. Preferably blades 42 and 43 are arranged for snap fit engagement and release as required. Typically blades 42 and 43 can be twisted on or off support side arms 8 and 9. Locking cap 24 has been placed over anchor pin 21.

Figure 7E:
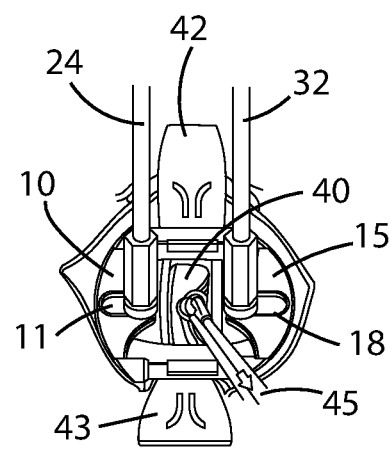

FIG. 7e shows frame 1 set over pins 21 and 26 obscured by respective tightening/locking caps 24 and 32. Once retractor blades 42 and 43 are set on support arms 8 and 9, locking caps 24 and 32 can be locked to retain a preselected extent of vertebral distraction. It can be seen that recesses 11 and 18 are elongated allowing movement of pins 21 and 26 in unison with movement of vertebra 27 and 28. This allows selective locking of the pins at any position along the recesses 11 and 18 to the plate once a desired extent of distraction is selected. This also allows angulation of the pins 21 and/or 26 where lordosis is required. FIG. 7e shows the arrangement of FIG. 7d with instrument 45 in disc space 40 engaged in superficial discectomy.

Figure 7F:
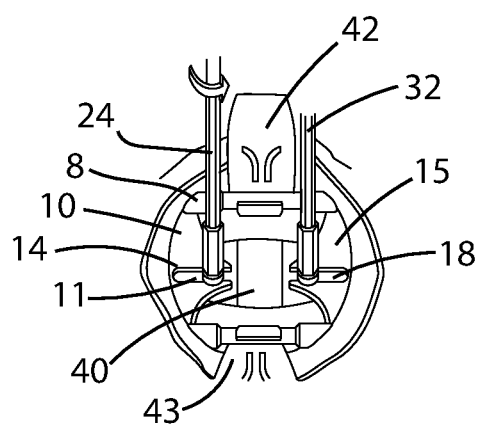
Figure 7G:
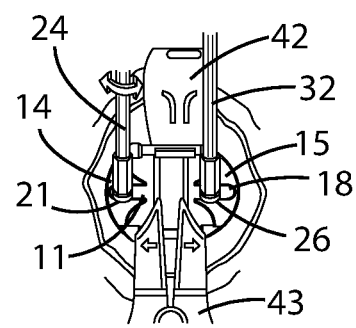

FIG. 7f shows in the arrangement of FIG. 7e with pins 21 and 26 at the original location relative to frame 1. To demonstrate locking after distraction, cap 24 over pin 21 is initially loosened allowing relative movement between pin 21 as distractor instrument 46 distracts vertebrae 27 and 28. As shown in FIG. 7g, pin 21 has been distracted in unison with vertebrae 27 to the limit of its travel to closed end 14 of recess 11. Cap 24 is tightened to secure pin 21 against frame 1. As shown in FIG. 7j, if more distraction is required, pin 26 can after loosening cap 32 be re positioned in a similar manner as described for pin 21. It will be appreciated that either of anchor pins/screws 21 or 26 can be re positioned anywhere along respective recesses 11 and 18 depending upon the extent of distraction required. During this process retractor blades 42 and 43 will be unaffected since it is only the pins 21 and 26 which are fixed in vertebrae 27 and 28 that undergo distraction under the action of distraction instrument 45. The ability to selectively lock the distraction at a selected position within a range of possible positions allows unimpeded access to the operating site and improved angled access. Once a preferred graft, cage of total disc replacement is completed, the distraction frame 1 can be removed allowing fusion of discs 27 and 28 via a fusion plate (see FIGS. 8a & b).

Figure 8A:
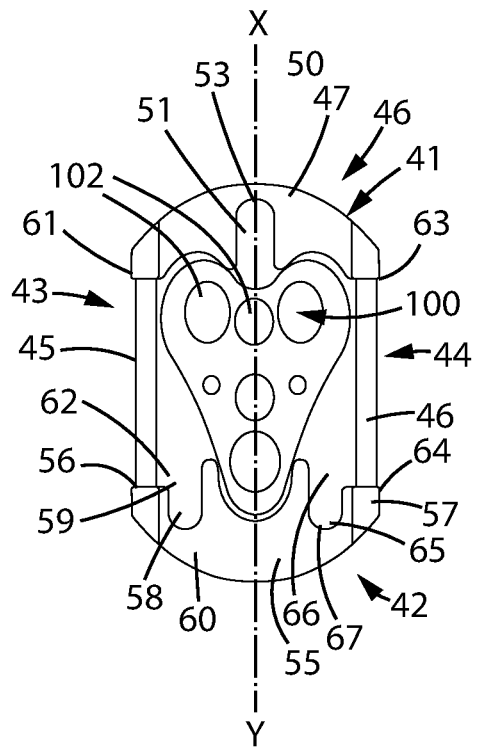
FIG. 8a shows a plan view of a frame device according to an alternative embodiment and which includes abutments on the side arms configured to accommodate a fusion plate.
Figure 8B:
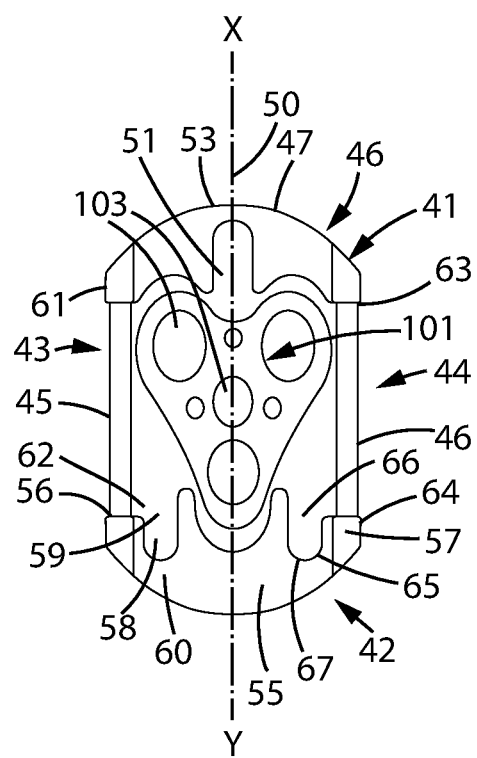
FIG. 8b shows a plan view of the frame device of FIG. 8a including an alternative fusion plate accommodated in the internal space defined by the frame.

FIGS. 8a & 8b show an enlarged plan view of a frame device 46 of the lockable distraction assembly according to an alternative embodiment. Frame 46 is in use, anchored to bone to set distraction once engaged with anchor pins to be described earlier. Frame 46 comprises a first pair of opposing sides 41 and 42 and a second pair of opposing sides 43 and 44 which comprise retractor blade support arms 45 and 46. Side 41 includes a bridge 47 which terminates at first and second abutments 48 and 49 which respectively engage retractor support arms 45 and 46. Bridge 47 further comprises an elongated recess 50 having one end 51 open to internal space 52 and a closed end 53 which provides when frame 46 is in use, a limiting abutment for an anchor pin. Side 42 includes a bridge 55 which terminates at first and second abutments 56 and 57 which respectively engage retractor support arms 45 and 46. Bridge 55 further comprises an elongated recess 58 having one end 59 open to internal space 52 and a closed end 60 which also provides when frame 40 is in use, a limiting abutment for an anchor pin. Retractor support arm 45 is provided with opposite end abutments 61 and 62. Retractor support arm 46 is provided with opposite end abutments 63 and 64. These abutments restrain lateral movement of retractor blades when connected to retractor support arms 45 and 46. Bridge 55 further comprises an elongated recess 65 having one end 66 open to internal space 52 and a closed end 67 which also provides when frame 40 is in use, a limiting abutment for an anchor pin. Intermediate recess 58 and 65 is an enlarged recess 70 which is arranged to accommodate therein at least part of an anchor/fusion plate 95. Preferably the device co-operates with two bone anchoring pins. The closed end of each said recesses provides a limiting abutment for the anchor pins enabling setting of a degree of distraction and/or degree of lordosis. Preferably the frame is generally planar and includes an interior space sufficient to provide surgical access and according to one embodiment, space to receive a fusion plate while the frame is in situ. As described, locking of the frame is effected by clamping between a bearing flange on each anchor pin and a tightening nut which is tightened against an upper surface of the first side arms.

The frame device 46 and which includes abutments on the retractor support arms and geometry to accommodate respective fusion plates 100 and 101 with alternative fixation configurations. Plate 100 includes an array of openings 102 which allow options for screw fixation. Plate 101 includes an alternative array of openings 103. It will be appreciated that the arrangement of openings 102 is flexible and a matter of deigns choice. Preferably the frame is generally planar and includes an interior space sufficient to provide surgical access and according to one embodiment, space to receive a fusion plate (100 and 101) while the frame is in situ.

FIG. 8 shows a plan view of a surgical site in which is located a distraction frame 40 retractor blades 42 and 43 and fusion plate 95.

Distractor frames 1 or 46 are positioned as required and secured with the bone screws. The standard discectomy procedure is performed until room for a standard intervertebral distracter assembly is created. The anchorage frame 1 is initially unlocked before the anchor pins are tightened via hex tools 24 and 32. While unlocked a conventional intervertebral scissor type distracter is used to effect distraction of vertebra. Once the desired amount of distraction is achieved usually about 8 mm, the anchorage frame 1/40 is locked which ensure that the vertebral bodies distracted. The intervertebral distracter is removed and the rest of the procedure completed. After insertion of a prosthesis (or at any point if so desired) the lock members 24 and 32 can be released to allow release of distraction force.

Variations in the anchorage frame may be made to accommodate different variation in anatomy. For instance the length, width and relative heights of horizontal and/or vertical sections, may vary to accommodate, different locations in the spine and different types of procedures. The corners of the frame may be radiused and in the lumbar spine build up sections over the corners added in order to retract blood vessels. The anchorage frame 2 is preferably wide enough to accommodate standards cages, bone grafts, plates and prosthesis etc. For the cervical region one screw hole (11 and 20) in respective parts 3 and 4 of frame 2 is expected to be sufficient in the cervical region whereas two screw holes may be required in the lumbar spine. A more complex oval shape frame combining curves and straight sections is also envisaged to accommodate surgery in other areas. The assembly described above may be employed in other functions such as but not limited to spinal deformity correction. For this function the anchorage frame 1/46 would be secured to one or two vertebral bones with the intention of reducing an adjacent bone such as an intermediate vertebra back to its normal aligned anatomical position; e.g. in grade 1 spondylolisthesis in the cervical spine. This could be done with oval shaped ends with the distracter locking engaged to prevent movement or with a circular frame end with or without distraction lock.

The assembly according to the present invention causes reduction of rotation or other unwanted movements. By having the frame tightly connected to the screws and bodies frame 1 is lockable against the pins with movement available by unlocking and restrained by locking.

The distracter lock describe herein imparts a number of advantages. Firstly the distracter is employed to maintain distraction by locking. Having the lock on the frame within the wound at or close to the plane in which the restoring forces are being resisted avoids the mechanical disadvantage with long lever arms of the other screw based mechanisms. The internal anchorage frame also potentially avoids bulky external mechanism that impede tools, hands and light as in the prior art assemblies. Although the frame lies within the wound it surrounds, it allows access to the critical working area. By being at or even below the bony surface, it does not impede the entry and exit of instruments and light. The frame may also be used with or without its associated retraction instruments.

It is also considered that the frame could be used as a compression lock device in order to maintain controlled compression. Compression could be applied to bones with tools attached to bone screws used to attach frame to bone or by other compressive mechanism.

Although described as a method for maintaining distraction in the spine or reducing mild deformity in the spine, it is contemplated that the assembly has additional applications in fracture reduction and fixation. The principle in its broadest form is one of internal fixation of a device using bone screws or pins attaching an internal frame capable of movement in a constrained way. In a general bone fracture and reduction setting, the frame could aid reduction as described in principle above but the locking feature could prevent separation of the bone elements once reduced. The locking feature could also be made to allow very small degrees of movement i.e. micro motion in the desired plane. The assembly may also have applications in other areas of surgery involving fractured bones for example craniofacial surgery and orthopaedics. Devices could be left in situ internally or removed after definitive fixation or healing.

It will be appreciated by those skilled in the art that the utilisation of this principal could be used in numerous other applications adapting to the different anatomy and retraction requirements throughout the spine, musculoskeletal system or wherever bony fixation can be utilised, e.g. the head.

It will be further recognised by persons skilled in the art that numerous variations and modifications may be made to the invention without departing from the overall spirit and scope of the invention broadly described herein. Such modifications would allow adaptation of key concepts to provide locking of distraction devices for use in anterior or posterior spinal surgery throughout the length of a spine or in orthopaedics or other surgical disciplines where bony fixation is available.

What is claimed:

1. A device for use in a surgical distraction and retraction assembly, the assembly including the device and at least one bone anchoring pin for securing the device against a bearing surface; characterized in that the device comprises: an integral frame defining an internal space, the frame having a first pair of opposing side arms and a second pair of opposing side arms; at least one of said side arms of said first pair of opposing side arms including at least one recess each having one of its ends open to the internal space defined by the frame and an opposite closed end terminating within said at least one side arm; each said recess retaining one said at least one bone anchoring pin and configured to enable relative movement between the frame and the bone anchoring pins; the relative movement allowing locking of said at least one anchor pin against the frame at a user selected location to maintain a selected extent of vertebral distraction.

2. A device according to claim 1 wherein the relative movement allowed between the frame and the bone anchoring pins is along a direction parallel to a longitudinal axis of each said second pair of side arms.

3. A device according to claim 2 wherein each side arm of said first pair of side arms has one said recess.

4. A device according to claim 3 wherein each recess is arranged as an elongated slot which retains one said bone anchoring pin.

5. A device according to claim 4 wherein the slots enable the relative movement between the frame and the bone anchoring pins.

6. A device according to claim 5 wherein each of said second pair of opposing side arms are arranged to retain a retractor.

7. A device according to claim 6 wherein the retractor is capable of movement relative to and detachable attachment to and from the each said second pair of side arms.

8. A device according to claim 7 wherein the retractor is rotatable about an axis through the side arm to which it is attached.

9. A device according to claim 8 wherein the elongated slots lie parallel to orientation of the second pair of side arms.

10. A device according to claim 9 wherein the closed end of each recess provides a limiting abutment for the anchor pins enabling setting of a degree of distraction and/or degree of lordosis.

11. A device according to claim 10 wherein the frame is locked in position by clamping between a bearing flange on each anchor pin and a tightening nut which is tightened against an upper surface of one or both first side arms.

12. A device according to claim 11 wherein the frame is generally planar and the internal space is large enough to provide surgical access to an operation site.

13. A device according to claim 1 wherein one of said first pair of side arms has one recess and the other of said first pair of side arms has two recesses of the same size.

14. A device according to claim 13 wherein the other side arm also includes a third recess larger than the two recesses.

15. A device according to claim 14 wherein the two recesses of the same size accommodate an anchor pin and the third larger recess accommodates at least part of a fusion plate insertable into the internal space.

16. A frame device for use in a surgical distraction and retraction assembly, the assembly including the frame device and at least two bone anchoring pins for securing the frame against a bearing surface on said at least two pins; characterized in that the frame device comprises: a first pair of opposing side arms and a second pair of opposing side arms together defining an internal space; each said side arms of said first pair of opposing side arms including at least one recess having one of its ends open to the internal space and an opposite closed end; at least one of each said recesses on each of the first pair of opposing sides receiving at least one of said at least one bone anchoring pins and enabling locking of said frame device against said at least two anchor pins to maintain a selected degree of vertebral distraction.

17. A frame device according to claim 16 wherein said locking is effected by a locking nut inducing compression between each side arm of the first pair of side arms of the frame and said anchor pins.

* * * * *